US009181393B2

(12) United States Patent
Bailey et al.

(10) Patent No.: US 9,181,393 B2
(45) Date of Patent: Nov. 10, 2015

(54) BIORENEWABLE BIODEGRADABLE SURFACTANTS

(75) Inventors: Brad C. Bailey, Midland, MI (US); Sze-Sze Ng, Midland, MI (US); Cynthia Pierre, Midland, MI (US); Cynthia L. Rand, Sanford, MI (US)

(73) Assignee: Dow Global Technologies, LLC, Midland, MI (US)

( * ) Notice: Subject to any disclaimer, the term of this patent is extended or adjusted under 35 U.S.C. 154(b) by 0 days.

(21) Appl. No.: 14/239,206

(22) PCT Filed: Aug. 16, 2012

(86) PCT No.: PCT/IB2012/002120
§ 371 (c)(1),
(2), (4) Date: Feb. 17, 2014

(87) PCT Pub. No.: WO2013/024363
PCT Pub. Date: Feb. 21, 2013

(65) Prior Publication Data
US 2014/0200353 A1 Jul. 17, 2014

Related U.S. Application Data

(60) Provisional application No. 61/524,637, filed on Aug. 17, 2011.

(51) Int. Cl.
| | |
|---|---|
| *C07C 69/753* | (2006.01) |
| *C07D 209/58* | (2006.01) |
| *C08G 65/48* | (2006.01) |
| *C11D 1/74* | (2006.01) |
| *C11D 1/52* | (2006.01) |
| *C08G 65/14* | (2006.01) |
| *C08G 65/26* | (2006.01) |
| *C08G 65/333* | (2006.01) |

(52) U.S. Cl.
CPC .............. *C08G 65/48* (2013.01); *C07C 69/753* (2013.01); *C07D 209/58* (2013.01); *C08G 65/14* (2013.01); *C08G 65/2612* (2013.01); *C08G 65/33396* (2013.01); *C11D 1/526* (2013.01); *C11D 1/74* (2013.01); *C07C 2103/26* (2013.01)

(58) Field of Classification Search
CPC . C07C 69/753; C07C 2103/26; C07D 209/58
USPC ............................................... 560/1; 548/426
See application file for complete search history.

(56) References Cited

U.S. PATENT DOCUMENTS

| | | | |
|---|---|---|---|
| 3,076,022 A | 1/1963 | Kitchens et al. | |
| 3,965,186 A | 6/1976 | Hall et al. | |
| 5,268,489 A | 12/1993 | Koleske et al. | |
| 5,691,300 A | 11/1997 | Fabry et al. | |
| 7,368,419 B2 | 5/2008 | Boehme et al. | |
| 7,557,148 B2 | 7/2009 | Nishiguchi et al. | |
| 7,686,877 B2 | 3/2010 | Engelbrecht et al. | |
| 7,871,971 B1 | 1/2011 | Koester et al. | |
| 2006/0154846 A1 | 7/2006 | Wang | |
| 2010/0137649 A1 | 6/2010 | Scheibel et al. | |

FOREIGN PATENT DOCUMENTS

| | | |
|---|---|---|
| EP | 0 586 323 A1 | 3/1994 |
| EP | 1925607 A1 | 5/2008 |
| EP | 2014757 A1 | 1/2009 |
| GB | 896039 | 5/1962 |
| JP | 2000 143686 A | 5/2000 |
| WO | 82/04249 A1 | 12/1982 |
| WO | 89/11524 A1 | 11/1989 |
| WO | 2004/096965 A1 | 11/2001 |

OTHER PUBLICATIONS

Vippagunta, et al. Advanced Drug Delivery Reviews, 48, 2001, 3-26.*
Abate et al., "Unsaturated polyester containing myrcene-maleic anhydride diels-alder adduct" Journal of Applied Polymer Science (1992) vol. 46, pp. 389-391.
Marson et al., "Cyclic acid anhydrides as a new class of potent, selective and non-peptidic inhibitors of geranylgeranyl transferase" Bioorganic & Medicinal Chemistry Letters (2002), vol. 12, pp. 255-259.
Yamada et al., "Synthesis of (+)-Nanaimool from N,N-Diethlgeranylamine" Chemistry Letters (1993), pp. 29-30.
Dragan et al., "Synthesis of four racemic rosane diterpenes" Mendeleev Communications (1991) (vol. 1(1), pp. 36-37.
The International Search Report for PCT/IB2012/002120 dated Jan. 31, 2013.
The International Preliminary Report on Patentability for PCT/IB2012/002120 dated Feb. 27, 2014.

* cited by examiner

*Primary Examiner* — Shawquia Jackson
(74) *Attorney, Agent, or Firm* — McDonnell Boehnen Hulbert & Berghoff

(57) ABSTRACT

Disclosed are compounds of formula (I) and salts, hydrates, or solvates thereof, where $R_1$ and $R_2$ are defined herein, compositions containing these compounds, and methods of using these compounds in a variety of applications, such as a surfactant or performance additive.

18 Claims, 2 Drawing Sheets

BIORENEWABLE BIODEGRADABLE SURFACTANTS

CROSS-REFERENCE TO RELATED APPLICATIONS

This application is a U.S. national phase of International Application No. PCT/IB2012/002120, filed Aug. 16, 2012, which claims priority from U.S. Provisional Application No. 61/524,637, filed Aug. 17, 2011; the disclosures of both of these applications are incorporated herein by reference in their entireties.

BACKGROUND OF THE INVENTION

1. Field of the Invention

This disclosure relates to compounds and compositions suitable for use in automatic dishwashing detergent compositions. In particular, the disclosure relates to tricyclic compounds derived from farnesene.

2. Description of Related Art

The waste streams of automatic dishwashers can spill into groundwater. The potential for these waste streams to have deleterious effects on aquatic plant and animal life and groundwater quality leads to significant regulation. Recent legislation has mandated a reduction in phosphorous levels in automatic dishwashing (ADW) detergent formulations to trace levels. This has forced detergent formulators to remove all sources of phosphorus from their detergents. Phosphorus containing additives are excellent cleaning agents and their removal from detergent formulations adversely affects cleaning, food soil removal, food soil redeposition, and scale build-up.

Food soil removal and enhanced finishing (i.e., shine) are important customer requirements in the ADW industry. With the reformulation of ADW detergents, achieving these performance requirements has become more challenging. Surfactants can help close the performance gap that the removal of phosphorus containing materials has created by providing some of the functionality that those materials provided. One primary example is the ability of surfactants and polymers to serve as food soil dispersants, which assists in minimizing food soil redeposition. The large shift towards environmentally friendly formulations has resulted in the need for the industry to provide readily biodegradable and non-toxic surfactants and additives. Surfactants and additives with renewable content can be preferable to their synthetic counterparts with demand being driven by life sustainability initiatives, preferred buying programs and consumer trends. Currently, most commercially available surfactants with renewable content are derived from natural sources such as animal and/or vegetable fats and oils.

SUMMARY OF THE INVENTION

In a broad aspect, the disclosure provides compounds or mixtures thereof, and formulations containing said compounds that contain cyclic-branched hydrophobes, which may be derived from farnesene. These surfactants demonstrate superior cleaning capability in phosphorus-free Automatic Dishwashing (ADW) detergent formulations when compared to the leading incumbent technology. These surfactants also demonstrate potential for enhanced performance in rinse aid applications for ADW.

Thus, one aspect of the disclosure (embodiment 1) provides compounds of formula (I):

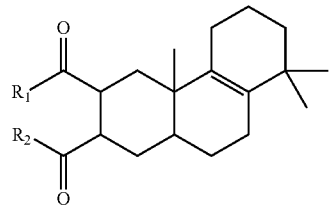

or regioisomers thereof, or salts, hydrates, or solvates thereof; wherein $R_1$ and $R_2$ are independently —$OR_5$, —$O^-M^+$, —$NHR_5$, or —$N(C_1$-$C_6$ alkyl)$R_5$;

where $R_5$ is hydrogen, $C_1$-$C_{20}$ alkyl, $C_2$-$C_{20}$ alkenyl, $C_2$-$C_{20}$ alkynyl, or a polyoxyalkylene moiety having oxyalkyl groups that are the same or different, and can be capped or uncapped, and where $M^+$ is a cation forming a salt; or $R_1$ and $R_2$ together form a group of formula:

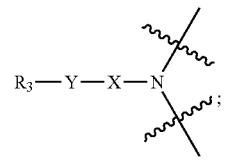

$R_3$ is hydrogen, $C_1$-$C_{20}$ alkyl, $C_2$-$C_{20}$ alkenyl, $C_2$-$C_{20}$ alkynyl, or a polyoxyalkylene moiety having oxyalkyl groups that are the same or different (and can be capped or uncapped), or $R_3$ is —Z—$R_4$:

wherein Z is $C_1$-$C_{20}$ alkylene, $C_2$-$C_{20}$ alkenylene, $C_2$-$C_{20}$ alkynylene, or a polyoxyalkylene moiety having oxyalkyl groups that are the same or different (and can be capped or uncapped) and $R_4$ is a group of the formula:

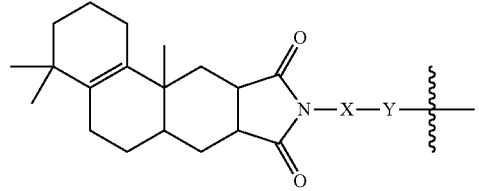

X is independently $C_1$-$C_6$ alkylene, $C_2$-$C_6$ alkenylene, or $C_2$-$C_6$ alkynylene, each optionally substituted with halogen, —OH, $C_1$-$C_6$ alkoxy, —$NO_2$, —CN, —$NH_2$, —NH($C_1$-$C_6$ alkyl), or —$N(C_1$-$C_6$ alkyl)$_2$; and Y is independently —O—, —NH—, —$N(C_1$-$C_6$ alkyl)-, —C(O)—, —C(O)O—, —C(O)NH—, —$C(O)N(C_1$-$C_6$ alkyl)-, —$S(O)_2$—, or —$S(O)_2O$—.

The disclosure also provides intermediates that are useful in making the compounds of formula (I).

The disclosure also provides methods of preparing compounds of the disclosure and the intermediates used in those methods.

The disclosure also provides compositions comprising a compound of formula (I) or mixtures thereof, and at least one additive, excipient or diluent.

The disclosure also provides cleaning compositions comprising a compound of formula (I) or mixtures thereof. Such compositions include both detergent and rinse aid compositions for Automatic Dishwashing (ADW) applications.

The disclosure further provides uses of the compounds and compositions of the disclosure as surfactants.

Also, the disclosure provides a method of using the compounds and the compositions of the disclosure in Automatic Dishwashers or formulations.

DETAILED DESCRIPTION OF THE INVENTION

Figure 1:
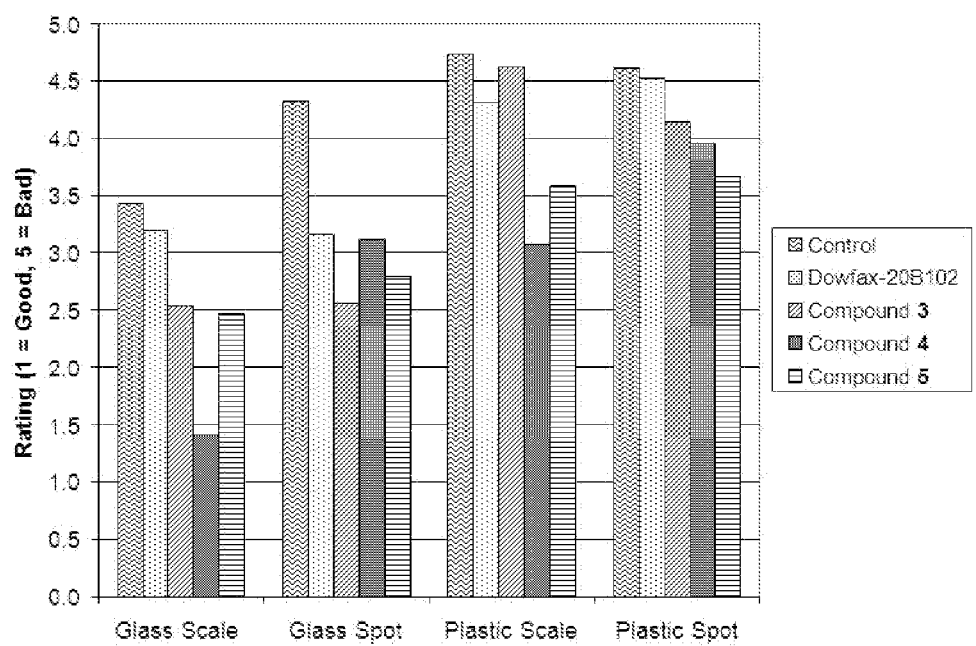
FIG. 1. Automatic dishwashing (ADW) performance in a detergent formulation of Compound 3, Compound 4, and Compound 5 for glass scale, glass spot, plastic scale, and plastic spot.

In embodiment 2, the disclosure provides compounds of embodiment 1 wherein $R_1$ and $R_2$ are independently —$OR_5$, —$O^-M^+$, —$NHR_5$, or —$N(C_1$-$C_6$ alkyl)$R_5$; where $R_5$ is hydrogen, $C_1$-$C_{20}$ alkyl, $C_2$-$C_{20}$ alkenyl, $C_2$-$C_{20}$ alkynyl, or a polyoxyalkylene moiety having oxyalkyl groups that are the same or different (and can be capped or uncapped), and where $M^+$ is a cation forming a salt.

In embodiment 3, the disclosure provides compounds of embodiment 2 wherein $R_1$ and $R_2$ are independently —$OR_5$, —$O^-M^+$, or —$NHR_5$, where $R_5$ is hydrogen, $C_1$-$C_{20}$ alkyl, $C_2$-$C_{20}$ alkenyl, $C_2$-$C_{20}$ alkynyl, or a polyoxyalkylene moiety having oxyalkyl groups that are the same or different (and can be capped or uncapped), and where $M^+$ is a cation forming a salt.

In embodiment 4, the disclosure provides compounds of embodiment 2 wherein $R_1$ and $R_2$ are independently —$OR_5$ or —$O^-M^+$, and where $R_5$ is hydrogen, $C_1$-$C_{20}$ alkyl, $C_2$-$C_{20}$ alkenyl, $C_2$-$C_{20}$ alkynyl, or a polyoxyalkylene moiety having oxyalkyl groups that are the same or different (and can be capped or uncapped), and where $M^+$ is a cation forming a salt.

Embodiment 5 provides compounds of embodiment 4 wherein $R_1$ and $R_2$ are both —$OR_5$ and $R_5$ is hydrogen, $C_1$-$C_6$ alkyl, or a polyoxyalkylene moiety having oxyalkyl groups that are the same or different, and can be capped or uncapped.

Embodiment 6 provides compounds of embodiment 4 wherein $R_1$ and $R_2$ are independently —$OR_5$ or —$O^-M^+$, and $R_5$ is hydrogen, and $M^+$ is a cation forming a salt. In embodiment 7, $R_1$ and $R_2$ are both —$OR_5$, and $R_5$ is hydrogen. In a separate embodiment 8, one or both of $R_1$ and $R_2$ is —$O^-M^+$, and $M^+$ is a cation forming a salt.

Embodiment 9 provides compounds of any one of embodiments 1-5 wherein $R_5$ is a polyoxyalkylene moiety having oxyalkyl groups that are the same or different, and can be capped or uncapped. In embodiment 10, the polyoxyalkylene moiety is polyoxymethylene, polyethylene glycol (i.e., polyoxymethylene), methoxypolyethylene glycol (i.e., methoxypolyoxyethylene), polypropylene glycol (i.e., polyoxypropylene), polytetramethylene glycol (i.e., polyoxytetramethylene), or a combination thereof. In embodiment 11, the polyoxyalkylene moiety is polyethylene glycol, methoxypolyethylene glycol, polypropylene glycol, or a combination thereof. Embodiment 12 provides compounds according to any preceding embodiment where the polyoxyalkylene moiety is polyethylene glycol or methoxypolyethylene glycol.

In embodiment 13, the disclosure provides compounds of any one of embodiments 1-12 wherein polyoxyalkylene moiety (e.g., polyethylene glycol or methoxypolyethylene glycol) has a molecular weight between about 100 and about 5000. In embodiment 14, the molecular weight is between about 300 and about 3500. In embodiment 15, the molecular weight is between about 300 and about 1000.

Embodiment 16 provides compounds of embodiment 1 wherein $R_1$ and $R_2$ together form a group of formula:

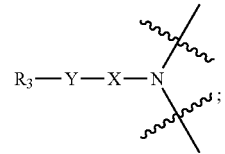

where $R_3$ is hydrogen, $C_1$-$C_{20}$ alkyl, $C_2$-$C_{20}$ alkenyl, $C_2$-$C_{20}$ alkynyl, or a polyoxyalkylene moiety having oxyalkyl groups that are the same or different, or $R_3$ is —Z—$R_4$:
wherein Z is $C_1$-$C_{20}$ alkylene, $C_2$-$C_{20}$ alkenylene, $C_2$-$C_{20}$ alkynylene, or a polyoxyalkylene moiety having oxyalkyl groups that are the same or different (and can be capped or uncapped) and $R_4$ is a group of the formula:

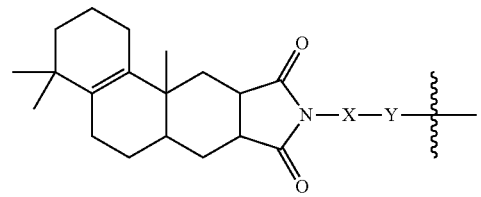

X is independently $C_1$-$C_6$ alkylene, $C_2$-$C_6$ alkenylene, or $C_2$-$C_6$ alkynylene, each optionally substituted with halogen, —OH, $C_1$-$C_6$ alkoxy, —$NO_2$, —CN, —$NH_2$, —NH($C_1$-$C_6$ alkyl), or —N($C_1$-$C_6$ alkyl)$_2$; and Y is independently —O—, —NH—, —N($C_1$-$C_6$ alkyl)-, —C(O)—, —C(O)O—, —C(O)NH—, —C(O)N($C_1$-$C_6$ alkyl)-, —S(O)$_2$—, or —S(O)$_2$O—.

Embodiment 17 provides compounds of embodiment 16 wherein where $R_1$ and $R_2$ together form a group of formula:

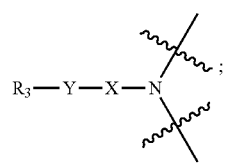

where $R_3$ is hydrogen, $C_1$-$C_{20}$ alkyl, $C_2$-$C_{20}$ alkenyl, $C_2$-$C_{20}$ alkynyl, or a polyoxyalkylene moiety having oxyalkyl groups that are the same or different, and can be capped or uncapped;

X is independently $C_1$-$C_6$ alkylene, $C_2$-$C_6$ alkenylene, or $C_2$-$C_6$ alkynylene, each optionally substituted with halogen, —OH, $C_1$-$C_6$ alkoxy, —$NO_2$, —CN, —$NH_2$, —NH($C_1$-$C_6$ alkyl), or —N($C_1$-$C_6$ alkyl)$_2$; and Y is independently —O—, —NH—, —N($C_1$-$C_6$ alkyl)-, —C(O)—, —C(O)O—, —C(O)NH—, —C(O)N($C_1$-$C_6$ alkyl)-, —S(O)$_2$—, or —S(O)$_2$O—.

In embodiment 18, the disclosure provides compounds of embodiment 16 or 17 wherein X is $C_1$-$C_6$ alkylene, $C_2$-$C_6$ alkenylene, or $C_2$-$C_6$ alkynylene. In embodiment 19, X is $C_1$-$C_6$ alkylene. In embodiment 20, X is methylene.

In embodiment 21, the disclosure provides compounds of any one of embodiments 1-20 wherein Y is —O—, —NH—, —N($C_1$-$C_6$ alkyl)-, —C(O)—, —C(O)O—, —C(O)NH—, or —C(O)N($C_1$-$C_6$ alkyl)-. In embodiment 22, Y is —O—, —NH—, —C(O)O—, or —C(O)NH—. In embodiment 23, Y is —C(O)O— or —C(O)NH—. Specifically, Y is —C(O)O— in embodiment 24.

Embodiment 25 provides compounds of embodiment 17 wherein X is $C_1$-$C_6$ alkylene; and Y is —O—, —NH—, —N($C_1$-$C_6$ alkyl)-, —C(O)—, —C(O)O—, —C(O)NH—, —C(O)N($C_1$-$C_6$ alkyl)-, —S(O)$_2$—, or —S(O)$_2$O—.

Embodiment 26 provides compounds of embodiment 17 wherein
X is $C_1$-$C_6$ alkylene optionally substituted with halogen, —OH, $C_1$-$C_6$ alkoxy, —NO$_2$, —CN, —NH$_2$, —NH($C_1$-$C_6$ alkyl), or —N($C_1$-$C_6$ alkyl)$_2$; and
Y is —C(O)—, —C(O)O—, —C(O)NH—, or —C(O)N($C_1$-$C_6$ alkyl)-.

Embodiment 27 provides compounds of embodiment 17 wherein X is $C_1$-$C_6$ alkylene; and Y is —C(O)—, —C(O)O—, —C(O)NH—, or —C(O)N($C_1$-$C_6$ alkyl)-.

Embodiment 28 provides compounds of embodiment 17 wherein X is $C_1$-$C_6$ alkylene; and Y is —C(O)O—, or —C(O)NH—.

In embodiment 29, the disclosure provides compounds of any one of embodiments 17-28 wherein $R_3$ is hydrogen, $C_1$-$C_{20}$ alkyl, or a polyoxyalkylene moiety having oxyalkyl groups that are the same or different, and can be capped or uncapped.

In embodiment 30, the disclosure provides compounds of embodiment 29 wherein $R_3$ is hydrogen.

Embodiment 31 provides compounds of embodiment 29 wherein $R_3$ is a polyoxyalkylene moiety having oxyalkyl groups that are the same or different, and can be capped or uncapped.

Embodiment 32 provides the compounds of embodiment 31, where the polyoxyalkylene moiety is polyoxymethylene, polyethylene glycol, methoxypolyethylene glycol, polypropylene glycol, polytetramethylene glycol, or a combination thereof. In embodiment 33, the polyoxyalkylene moiety is polyethylene glycol, methoxypolyethylene glycol, polypropylene glycol, or a combination thereof. In embodiment 34, the polyoxyalkylene moiety is polyethylene glycol or methoxypolyethylene glycol.

In embodiment 36, the disclosure provides compounds of any one of embodiments 31-34 wherein the polyoxyalkylene moiety (e.g., polyethylene glycol or methoxypolyethylene glycol) has a molecular weight between about 100 and about 5000. In embodiment 37, the molecular weight is between about 300 and about 3500. In embodiment 38, the molecular weight is between about 300 and about 1000.

Embodiment 38 provides compounds of embodiment 16 wherein $R_3$ is —Z—$R_4$, and
Z is $C_1$-$C_{20}$ alkylene, $C_2$-$C_{20}$ alkenylene, $C_2$-$C_{20}$ alkynylene, or a polyoxyalkylene moiety having oxyalkyl groups that are the same or different; and $R_4$ is a group of the formula:

In embodiment 39, each X is independently $C_1$-$C_6$ alkylene, $C_2$-$C_6$ alkenylene, or $C_2$-$C_6$ alkynylene. In embodiment 40, each X is $C_1$-$C_6$ alkylene. In embodiment 41, each X is methylene. Embodiment 42 provides compounds according to any one of embodiments 38-41, where each Y is independently —O—, —NH—, —N($C_1$-$C_6$ alkyl)-, —C(O)—, —C(O)O—, —C(O)NH—, or —C(O)N($C_1$-$C_6$ alkyl)-. Another embodiment 43 provides compounds of embodiment 42 where each Y is independently —O—, —NH—, —C(O)O—, or —C(O)NH—. In embodiment 44, each Y is independently —C(O)O— or —C(O)NH—. More specifically, each Y is —C(O)O— in embodiment 45.

Embodiment 46 provides compounds of embodiment 38 wherein each X is $C_1$-$C_6$ alkylene; and each Y is independently —O—, —NH—, —N($C_1$-$C_6$ alkyl)-, —C(O)—, —C(O)O—, —C(O)NH—, —C(O)N($C_1$-$C_6$ alkyl)-, —S(O)$_2$—, or —S(O)$_2$O—.

Embodiment 47 provides compounds of embodiment 38 wherein each X is independently $C_1$-$C_6$ alkylene optionally substituted with halogen, —OH, $C_1$-$C_6$ alkoxy, —NO$_2$, —CN, —NH$_2$, —NH($C_1$-$C_6$ alkyl), or —N($C_1$-$C_6$ alkyl)$_2$; and each Y is independently —C(O)—, —C(O)O—, —C(O)NH—, or —C(O)N($C_1$-$C_6$ alkyl)-.

Embodiment 48 provides compounds of embodiment 47 wherein each X is $C_1$-$C_6$ alkylene; and each Y is independently —C(O)—, —C(O)O—, —C(O)NH—, or —C(O)N($C_1$-$C_6$ alkyl)-.

Embodiment 49 provides compounds of embodiment 38 wherein each X is $C_1$-$C_6$ alkylene; and each Y is independently —C(O)O—, or —C(O)NH—.

In embodiment 50, the disclosure provides compounds of embodiment 49 wherein each X is methylene; and each Y is —C(O)O—.

In embodiment 51, the disclosure provides compounds of any one of embodiments 38-50 wherein Z is $C_1$-$C_{20}$ alkylene, or a polyoxyalkylene moiety having oxyalkyl groups that are the same or different, and can be capped or uncapped. In embodiment 52, Z is $C_1$-$C_{20}$ alkylene.

In embodiment 53, compounds of embodiment 51 have Z that is a polyoxyalkylene moiety having oxyalkyl groups that are the same or different (and can be capped or uncapped). Specifically, the polyoxyalkylene moiety is polyoxymethylene, polyethylene glycol, polypropylene glycol, polytetramethylene glycol, or a combination thereof in embodiment 54. In embodiment 55, the polyoxyalkylene moiety is polyethylene glycol, polypropylene glycol, or a combination thereof. In embodiment 56, the polyoxyalkylene moiety is polyethylene glycol. Embodiment 57 provides compounds of any one of embodiments 53-56, where the polyoxyalkylene moiety (e.g., polyethylene glycol) has a molecular weight between about 100 and about 5000. In embodiment 58, the molecular weight is between about 300 and about 3500. In embodiment 59, the molecular weight is between about 300 and about 1000.

Compositions and Dosage

In another aspect, the present disclosure provides compositions comprising one or more compounds with respect to formula (I) and an additive, excipient or diluent. The exact nature of the additive, excipient or diluent will depend upon the desired use for the composition. Examples, include, but are not limited to: other cleaning agents (e.g. surfactants, co-surfactants), chelating agents, phosphate or non-phosphate builders, pH control agents, enzymes, enzyme stabilizing agents, surfactants, sequestrants, alkalinity sources, water softening agents, secondary solubility modifiers, thickeners, acids, soil release polymers, suds suppressors and defoamers, dispersant polymers, hydrotropes, antibacterial actives, ger-

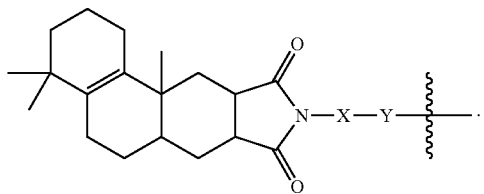

micides, abrasives, anti-redeposition agents, threshold agents or systems, bleaching agents, aesthetic enhancing agents (i.e., dyes, colorants, pigments, perfumes, etc.), oils, solvents, binders, fillers, carrier mediums, and mixtures thereof.

Suitable surfactants include anionic surfactants, cationic surfactants, nonionic surfactants, amphoteric surfactants, ampholytic surfactants, zwitterionic surfactants, and mixtures thereof. Non-limiting examples of anionic surfactants are alkyl sulfates, alkyl ether sulfates, alkyl benzene sulfonates, alkyl glyceryl sulfonates, alkyl and alkenyl sulphonates, alkyl ethoxy carboxylates, N-acyl sarcosinates, N-acyl taurates and alkyl succinates and sulfosuccinates, wherein the alkyl, alkenyl or acyl moiety is $C_5$-$C_{20}$, linear or branched. Non-limiting examples of cationic surfactants are chlorine esters and mono $C_6$-$C_{16}$ N-alkyl or alkenyl ammonium surfactants, wherein the remaining N positions are substituted by methyl, hydroxyethyl or hydroxypropyl groups. Non-limiting examples of nonionic surfactants include low and high cloud point surfactants, and low-foaming surfactants. Non-limiting examples of amphoteric surfactants include the $C_{12}$-$C_{20}$ alkyl amine oxides (e.g., lauryldimethyl amine oxide and hexadecyl dimethyl amine oxide), and alkyl amphocarboxylic surfactants, such as Miranol®. Suitable zwitterionic surfactants include betaines and sultaines; and mixtures thereof.

Suitable carrier mediums include both liquids and solids depending on the form of the composition desired. Solid carriers maybe used in dry powders, granules, tablets, encapsulated products, and combinations thereof. Liquid carries include water (distilled, deionized, or tap water), solvents, and mixtures thereof. The liquid carrier may also contain other materials which are liquid, or which dissolve in the liquid carrier at room temperature, and which may also serve some other function besides that of a carrier (e.g., dispersants, hydrotropes, and mixtures thereof.)

Suitable builders include, but are not limited to: citrate, phosphate (such as sodium tripolyphosphate, potassium tripolyphosphate, mixed sodium and potassium tripolyphosphate, sodium or potassium or mixed sodium and potassium pyrophosphate), aluminosilicate materials, silicates, polycarboxylates and fatty acids, materials such as ethylene-diamine tetraacetate, metal ion sequestrants such as aminopolyphosphonates, ethylenediamine tetramethylene phosphonic acid and diethylene triamine pentamethylene-phosphonic acid.

Non-limiting examples of enzymes include proteases, amylases, lipases, cellulases, peroxidases, and mixtures thereof. Amylases and/or proteases are commercially available with improved bleach compatibility.

Bleaching agents suitable for use include, but are not limited to: inorganic chlorine (such as chlorinated trisodium phosphate), organic chlorine bleaches (such as chlorocyanurates, water-soluble dichlorocyanurates, sodium or potassium dichloroisocyanurate dihydrate, sodium hypochlorite and other alkali metal hypochlorites), inorganic perhydrate salts (such as sodium perborate mono- and tetrahydrates and sodium percarbonate), sodium pyrophosphate peroxyhydrate, urea peroxyhydrate, sodium peroxide, and mixtures thereof.

The composition may optionally include one or more additional compounds.

The compound(s) described herein, or compositions thereof, will generally be used in an amount effective to achieve the intended result. Dosage amounts will typically be in the range of from about 0.1 to about 7 weight %, or about 3 weight %, or about 0.1 to about 30 weight %, but may be higher or lower, depending upon, among other factors, the activity as a surfactant, if the material is used as the main active surfactant and various other factors. Skilled artisans will be able to optimize effective dosages without undue experimentation.

Compositions may or may not contain phosphorus based molecules (e.g., sodium tripolyphosphate, STPP).

A composition of the disclosure may be used in any suitable product form. Suitable product forms include, but not limited to: solids, granules, powders, liquids, gels, pastes, semi-solids, tablets, water-soluble pouches, and combinations thereof. The composition may also be packaged in any suitable form, for example, in a kit.

A composition of the disclosure can be dispensed from any suitable device, including but not limited to: dispensing baskets or cups, bottles (pump assisted bottles, squeeze bottles, etc.), mechanic pumps, multi-compartment bottles, capsules, multi-compartment capsules, paste dispensers, and single- and multi-compartment water-soluble pouches, and the like. For example, a multi-phase tablet, a water-soluble or water-dispersible pouch, and combinations thereof, may be used to deliver the composition to any suitable solution or substrate. Suitable solutions and substrates include but are not limited to: hot and/or cold water, wash and/or rinse liquor, hard surfaces, and combinations thereof. The multi-phase product may be contained in a single or multi-compartment, water-soluble pouch. A composition may comprise a unit dose which allows for the controlled release (e.g., delayed, sustained, triggered, or slow release). The unit dose may be provided in any suitable form, including but not limited to: tablets, single- and multi-compartment water-soluble pouch, and the like. For example, the composition may be provided as a unit dose in the form of a multi-phase product comprising a solid (such as a granules or tablet) and a liquid and/or gel separately provided in a multi-compartment water-soluble pouch.

DEFINITIONS

The following terms and expressions used have the indicated meanings.

The term "alkenyl" as used herein, means a straight or branched chain hydrocarbon containing from 2 to 20 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkenylene" refers to a bivalent alkenyl group containing from 1 to 20 carbon atoms unless otherwise specified, and it may be a straight or branched chain.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 20 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" refers to a bivalent alkyl group containing from 1 to 20 carbon atoms unless otherwise specified, and it may be a straight or branched chain.

The term "alkynyl" as used herein, means a straight or branched chain hydrocarbon group containing from 2 to 10 carbon atoms unless otherwise specified, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "alkynylene" refers to a bivalent alkynyl group containing from 1 to 20 carbon atoms unless otherwise specified, and it may be a straight or branched chain. Examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—, etc.

The term "halogen" as used herein, means —Cl, —Br, —I or —F.

The term "polyoxyalkylene" refers to polymer moieties formed by polymerizing or copolymerizing alkylene oxide monomers to provide polymer moieties of desired size and weight, and the polymer moieties can be capped or uncapped. In general, the alkylene oxide monomers are independently straight or branched chain groups having from 1-6, preferably 2-5, carbon atoms. Where the polymer moiety comprises two or more polyoxyalkylene groups, the individual polyoxyalkylene groups may be connected to each other by linker groups. Examples of suitable linker groups are: —C(O)—, —O—, —O—C(O)O—, —C(O)CH$_2$CH$_2$C(O)—, —S—S—, and —NR$^3$—, where R$^3$ is hydrogen, or C$_1$-C$_6$ alkyl. Non-limiting examples of polyoxyalkylene groups include polyoxyethylene, a straight or branched chain polyoxypropylene, and a straight or branched chain polyoxybutylene. Polyoxyalkylene polymer moieties may have molecular weights of from about 200-10,000 Da; any of these moieties may be formed from several shorter, independently-sized units. The units may have molecular weights independently ranging from about 50 (i.e., one repeating unit of a polyethylene glycol), 200, or 500 Da up to about 3000, 4000 or 5000 Da.

"Salt" refers to both acid and base addition salts.

Certain compounds of this disclosure may exist as regioisomers; all such regioisomeric forms of the compounds are within the scope of the disclosure. Unless otherwise stated, structures depicted herein are also meant to include all regioisomeric forms of the structure. Therefore, single regioisomers as well mixtures of several regioisomers are within the scope of the disclosure. Regioisomers of compounds of formula (I) include, but are not limited to:

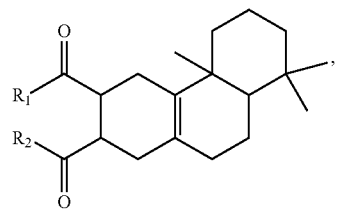,

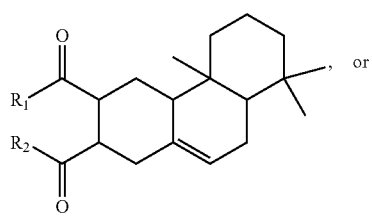, or

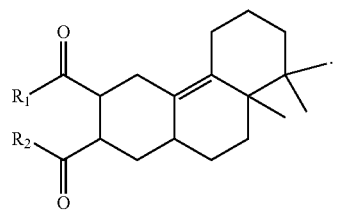.

Methods of Preparation

The compounds of the present disclosure may be prepared by use of known chemical reactions and procedures. Representative procedures for the preparation of compounds of the disclosure are outlined below in following schemes. It is understood that the nature of the substituents required for the desired target compound often determines the preferred method of synthesis. All variable groups of these methods are as described in the generic description if they are not specifically defined below.

Unless otherwise indicated, R$_1$, R$_2$, R$_3$, X, and Y, and carry the definitions given in connection with formula (I).

Scheme 1

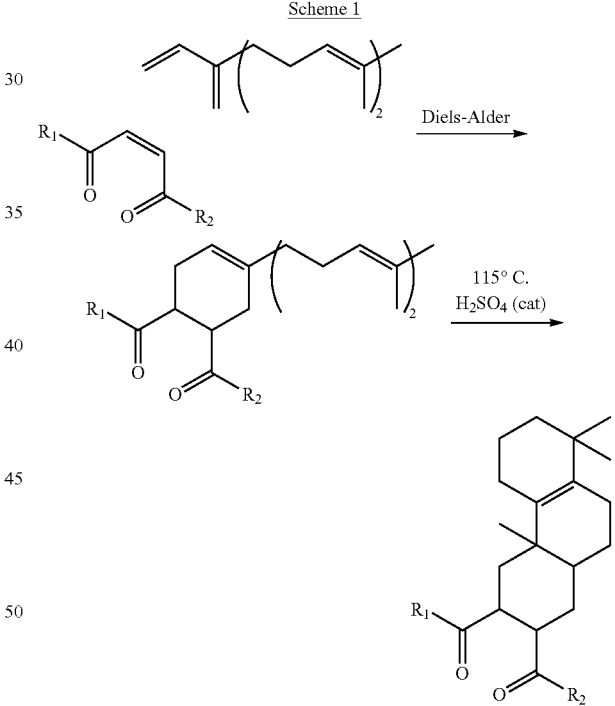

Scheme 2

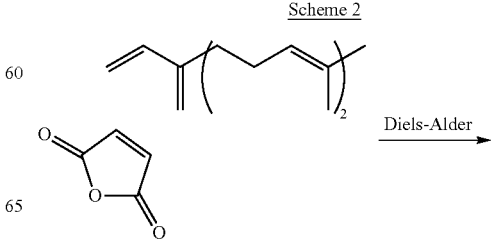

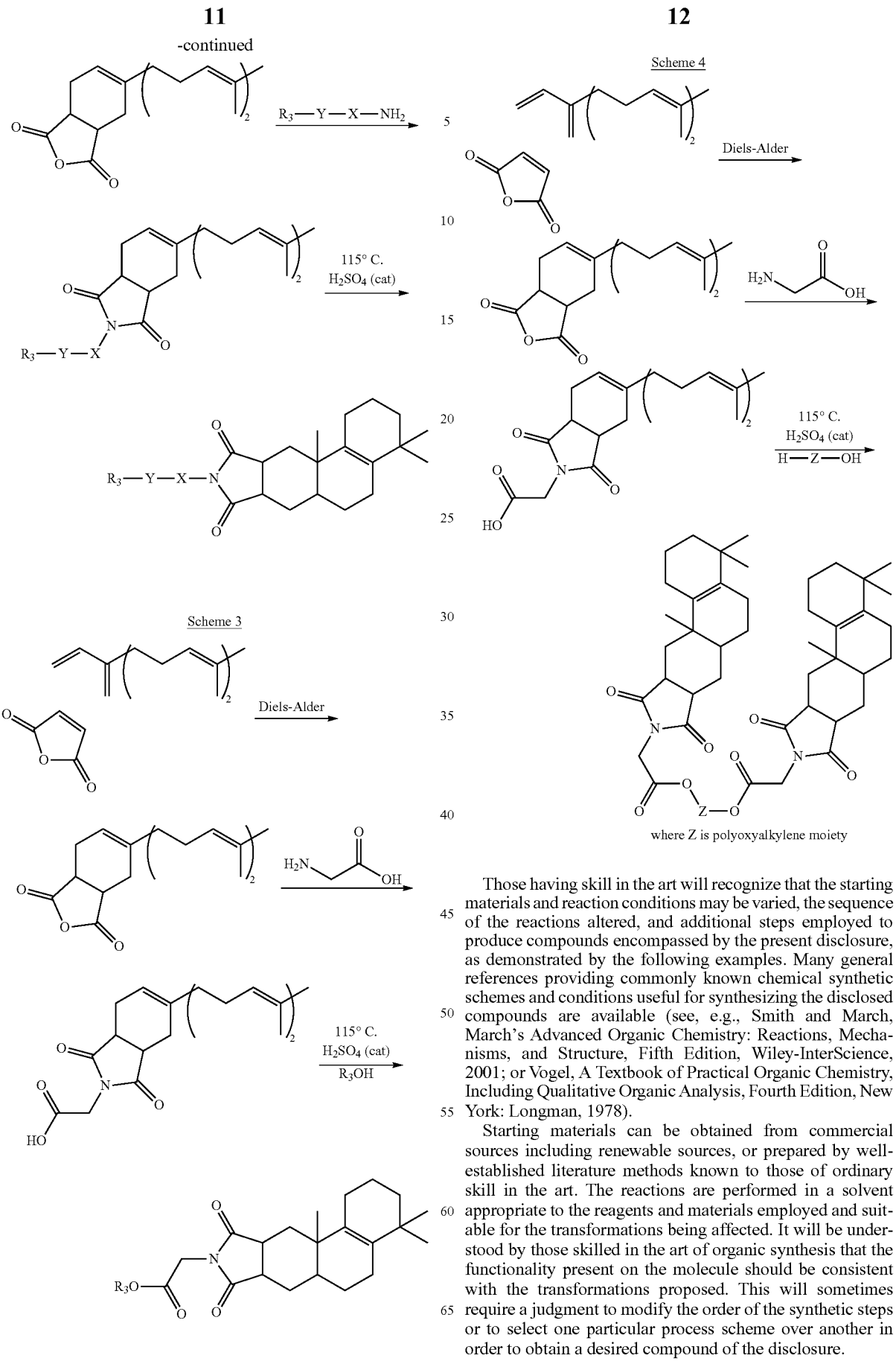

where Z is polyoxyalkylene moiety

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-InterScience, 2001; or Vogel, A Textbook of Practical Organic Chemistry, Including Qualitative Organic Analysis, Fourth Edition, New York: Longman, 1978).

Starting materials can be obtained from commercial sources including renewable sources, or prepared by well-established literature methods known to those of ordinary skill in the art. The reactions are performed in a solvent appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The disclosures of all articles and references mentioned in this application, including patents, are incorporated herein by reference in their entirety.

EXAMPLES

The preparation of the compounds of the disclosure is illustrated further by the following examples, which are not to be construed as limiting the disclosure in scope or spirit to the specific procedures and compounds described in them.

Example 1

Compound 1

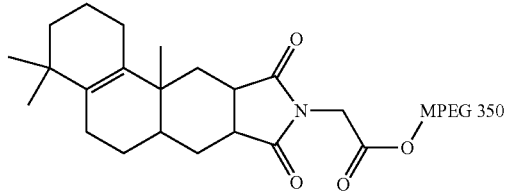

To a 50 mL round bottom flask {5-[4,8-dimethylnona-3,7-dien-1-yl]-1,3-dioxo-1,3,3a,4,7,7a-hexahydro-2H-isoindol-2-yl}acetic acid (1.00 g, 2.78 mmol, prepared as in Example 3), MPEG-350 (0.974 g, 2.78 mmol), and 5 drops of $H_2SO_4$ are added. The flask is purged with $N_2$ and heated to 100° C. for 4 hours. An aliquot of the crude mixture is taken and analyzed by GC, and no starting material remains. All volatiles are removed and checked by $^1H$ NMR. The crude material is collected without further purification (1.80 g, 94%). The crude material is readily soluble as an aqueous 1% solution.

Example 2

Compound 2

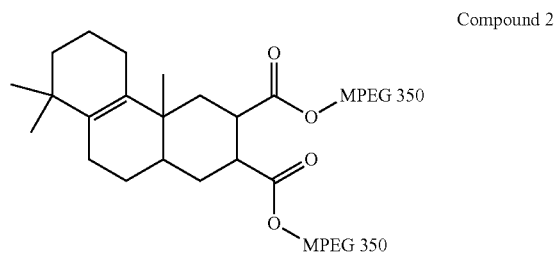

To a 50 mL round bottom flask 5-(4,8-dimethylnona-3,7-dien-1-yl)-3a,4,7,7a-tetrahydroisobenzofuran-1,3-dione (1.00 g, 3.31 mmol), MPEG-350 (2.32 g, 6.61 mmol), and 3 drops of $H_2SO_4$ (conc.) are added. The solution instantly turns to a black color once the $H_2SO_4$ is added. The round-bottom flask is equipped with septae and purged with $N_2$. The solution is heated to 110° C. for 16 hours. An aliquot of the crude mixture is taken and analyzed by GC, and no starting material remains. The crude material is collected and analyzed by NMR to give 2.70 g (87%). A 1% aqueous solution is prepared by adding 20 mg of the product into a dram vial followed by addition of 2 g of water. The solution is highly soluble as a 1% solution.

Example 3

Compound 3

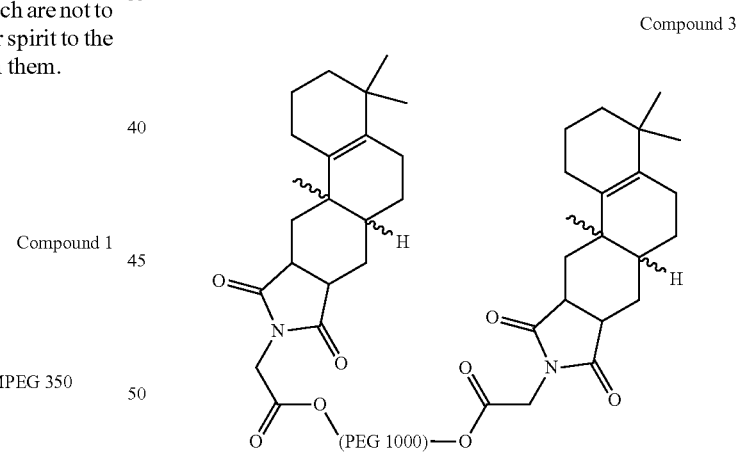

Step 1: Diels-Alder Reaction of β-farnesene and maleic anhydride:

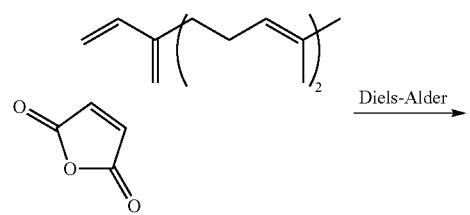

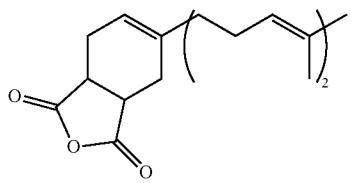

Maleic anhydride (4.80 g, 49 mmol) and toluene (~30 mL) is added to a 3-necked 100 mL round bottom flask equipped with a thermocouple, nitrogen inlet and an addition funnel. The flask is purged with $N_2$ and the funnel is charged with farnesene (10.00 g, 49 mmol). Farnesene is slowly added to the maleic anhydride/toluene solution at room temperature. Once addition of the farnesene is complete, the reaction mixture is heated to 65° C. and stirred for 2 hours to ensure completion of the reaction. The reaction mixture is then cooled to room temperature and the solvent is removed in vacuo to yield the product as a pale yellow viscous oil (14.65 g, 48 mmol, 99%).

Step 2: Addition of Glycine to the Diels-Alder Adduct

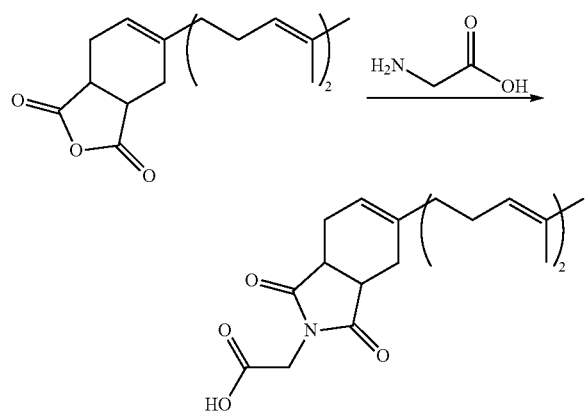

Diels-Alder adduct from the previous step (4.00 g, 13.2 mmol), glycine (0.99 g, 13.9 mmol) and about 20 mL of diglyme are added to a 50 mL round bottom flask equipped with a reflux condenser and a $N_2$ inlet. The reaction mixture is heated to 120° C. with a nitrogen purge for 24 h. The glycine slowly goes into solution to give a homogeneous pale yellow mixture. All volatiles are removed via vacuum distillation and the product, {5-[4,8-dimethylnona-3,7-dien-1-yl]-1,3-dioxo-1,3,3a,4,7,7a-hexahydro-2H-isoindol-2-yl}acetic acid is collected as a pale yellow, highly viscous oil (4.70 g, 13.1 mmol, 99%).

Step 3: Esterification with Polyethylene Glycol

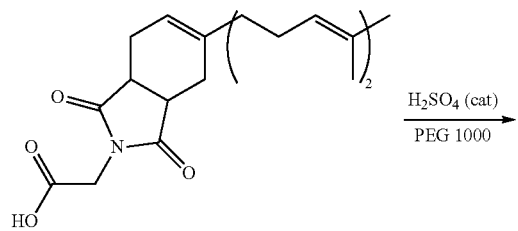

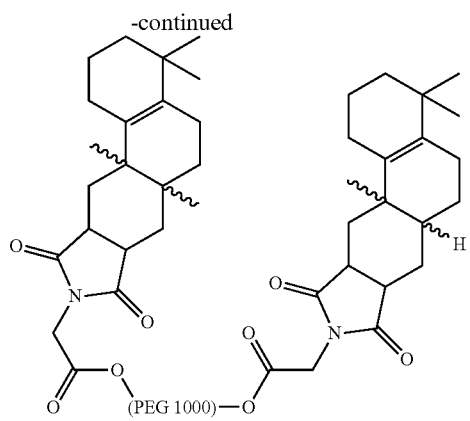

The product from the previous step, {5-[4,8-dimethylnona-3,7-dien-1-yl]-1,3-dioxo-1,3,3a,4,7,7a-hexahydro-2H-isoindol-2-yl}acetic acid (4.50 g, 12.52 mmol), PEG-1000 (6.26 g, 6.26 mmol), and 5 drops of $H_2SO_4$ are added to a 50 mL round bottom flask equipped with a $N_2$ inlet. The reaction mixture is heated to 100° C. with a nitrogen purge for 16 h. All volatiles are removed in vacuo and the product is collected as a pale yellow, highly viscous oil (10.52 g, 6.24 mmol, 99%).

Example 4

One-pot synthesis of Compound 3: Farnesene (3.00 g, 14.68 mmol), maleic anhydride (1.44 g, 14.68 mmol) and diglyme (15 mL) are added to a 50 mL round bottom flask. The reaction mixture is heated under nitrogen purge to 60° C. for 1 hour and then to 100° C. for 2 hours. The reaction mixture is cooled to room temperature, and glycine (1.10 g, 14.68 mmol) is added, placed under a nitrogen purge and heated to 60° C. for 2 days. After 2 d the reaction mixture is a clear orange solution. The reaction mixture is cooled to room temperature, and PEG1000 (7.34 g, 7.34 mmol) and $H_2SO_4$ (15 drops) are added, placed under a nitrogen purge and heated to 115° C. for 15 hours. The reaction mixture is cooled to room temperature, and a short path distillation apparatus is added to distill off diglyme. Compound 3 is collected as orange-brown viscous oil (99% yield).

Example 5

Compound 4

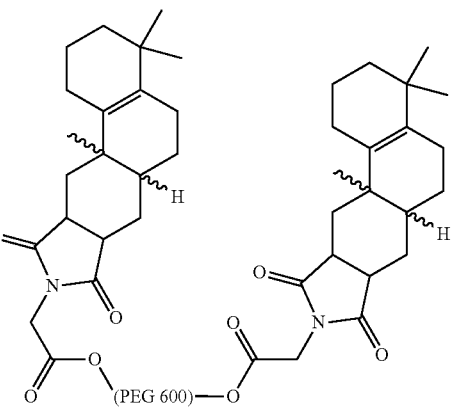

{5-[4,8-dimethylnona-3,7-dien-1-yl]-1,3-dioxo-1,3,3a,4,7,7a-hexahydro-2H-isoindol-2-yl}acetic acid (prepared as in the Example 3), PEG-600, and 5 drops of $H_2SO_4$ are added to a 50 mL round bottom flask equipped with a $N_2$ inlet. The reaction mixture is heated to 100° C. with a nitrogen purge for 16 h. All volatiles are removed in vacuo and the product is collected.

Example 6

Compound 5

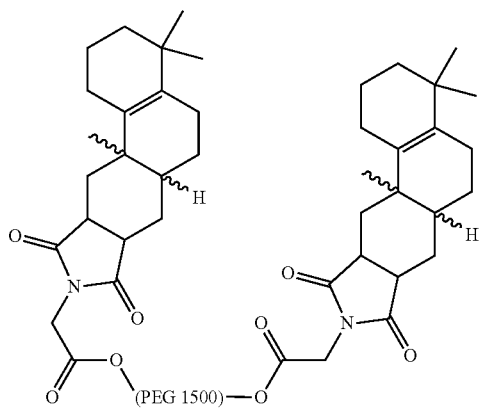

{5-[4,8-dimethylnona-3,7-dien-1-yl]-1,3-dioxo-1,3,3a,4,7,7a-hexahydro-2H-isoindol-2-yl}acetic acid (prepared as in the Example 3), PEG-1500, and 5 drops of $H_2SO_4$ are added to a 50 mL round bottom flask equipped with a $N_2$ inlet. The reaction mixture is heated to 100° C. with a nitrogen purge for 16 h. All volatiles are removed in vacuo and the product is collected.

Example 7

Automatic Dishwashing (ADW) Performance

Preparation of STIWA Food Soil: 25 g instant gravy, 5 g starch, and 1 g benzoic acid is mixed and added to 700 g of boiling tap water. 50 g milk (3.5% fat equivalent semi skimmed), and 100 g margarine are added to the mixture, and the mixture is cooled down to about 40° C. 25 g ketchup, 25 g mustard, and 3 g egg yolks are placed into the bowl of the kitchen machine (Polytron), and mixed using beating whisk. The cooled down mixture is added to the bowl, stirring continuously. The mixture is stirred for 5 minutes, and then frozen.

Test method: a modified version of ASTM D 3556-85 (Standard Test Method for Deposition on Glassware During Mechanical Dishwashing, 2009) is employed to evaluate the performance of the surfactants as components in ADW detergent formulations. The evaluation deviated from the standard test method by using STIWA food soil and by employing only 1 wash cycle with 3 glass and 3 plastic tumblers. The standard requires multiple cycles (5 to 15); however, only 1 cycle under extreme water hardness 300 ppm is employed, allowing the screening of a large number of surfactants. A 50 g sample of the frozen STIWA slush, as prepared above, is placed into the dishwasher prior to starting the test.

Evaluation and Results: A conventional light box as described in the standard is used to evaluate the tumblers. The light box contains black interior surfaces and fluorescent lights which are mounted in the base of the box. Light passes up through the tumblers during analysis and five tumblers can be analyzed simultaneously. The tumblers are rated separately for scale and spot formation both on a scale from 1 to 5. For scale formation, a rating of 1 corresponds to a clean tumbler without any deposition and a rating of 5 corresponds to a heavily filmed tumbler. For spot formation, a rating of 1 corresponds to a tumbler without any spots and a rating of 5 corresponds to a tumbler that is practically covered with spots. FIG. 1 illustrates results for glass scale, glass spot, plastic scale, and plastic spotting for Compound 3, 4, and 5, compared to a leading internal commercial technology (Dowfax-20B102).

Example 8

Surface Tension and Critical Micelle Concentration

Surface tension was measured using a Kibron Delta-8 microtensiometer. Kibron microtensiometer measured surface tension by maximum pull force/du Nouy method. The instrument is calibrated using Nanopure water. The 8 channel wire probes are cleaned internally in the instrument by heating. Sample volume for each analysis is 50 µL. For each sample, twelve dilutions starting at 1 wt % are prepared, reducing the concentration in each dilution by half by taking an aliquot of the previous dilution and adding the same amount of water. Hence, for each sample, surface tension at 12 different concentrations is recorded. From the surface tension data, critical micelle concentration (CMC) can be derived. CMC is the lowest concentration of a surfactant at which the minimum surface tension in water is achieved.

Figure 2:
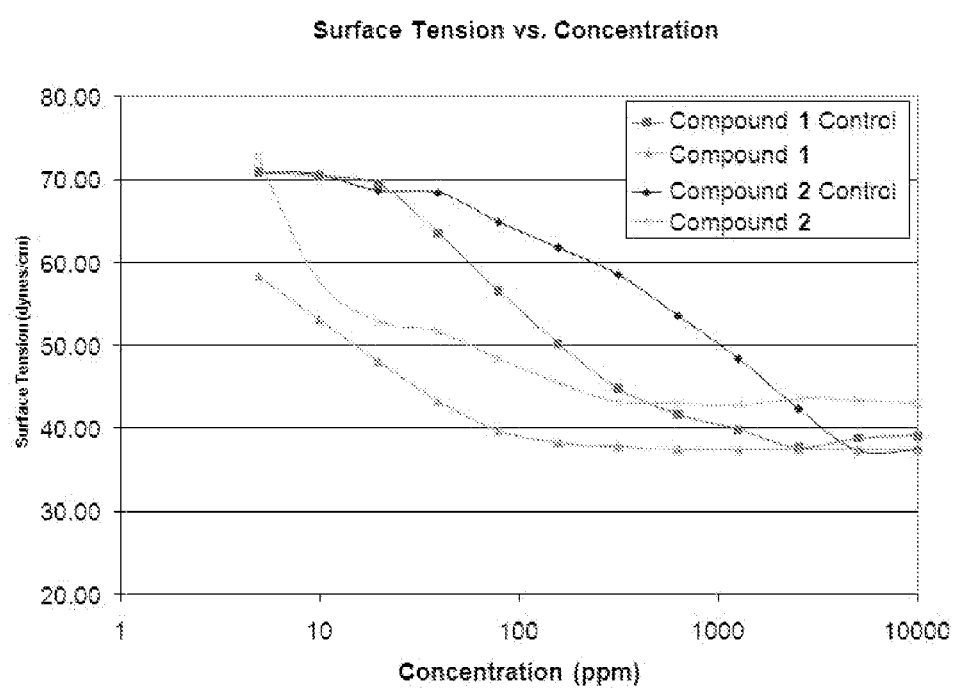
FIG. 2. Kibron Delta-8 Microtensiometer measurements of Compound 1 and Compound 2.

Surface tension data at different concentrations for compound 1, compound 2, and their controls are summarized in FIG. 2. Compound controls are Diels-Alder precursors, prior to acid catalyzed cationic cyclization reaction. In particular, Compound 1 Control is 4-(4,8-dimethylnona-3,7-dienyl)cyclohex-4-ene-1,2-dicarboxylic acid disodium salt; and Compound 2 Control is {5-[4,8-dimethylnona-3,7-dien-1-yl]-1,3-dioxo-1,3,3a,4,7,7a-hexahydro-2H-isoindol-2-yl}acetic acid sodium salt.

It is understood that the examples and embodiments described herein are for illustrative purposes only. Unless clearly excluded by the context, all embodiments disclosed for one aspect of the invention can be combined with embodiments disclosed for other aspects of the invention, in any suitable combination. It will be apparent to those skilled in the art that various modifications and variations can be made to the present invention without departing from the scope of the invention. Thus, it is intended that the present invention cover the modifications and variations of this invention provided they come within the scope of the appended claims and their equivalents. All publications, patents, and patent applications cited herein are hereby incorporated herein by reference for all purposes.

What is claimed is:

1. A compound of formula:

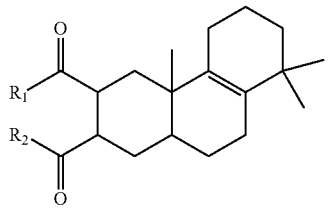

or a regioisomer or salt thereof; wherein
$R_1$ and $R_2$ are independently —$OR_5$, —$O^+M^+$, —$NHR_5$, or —$N(C_1$-$C_6$ alkyl)$R_5$;
where $R_5$ is hydrogen, $C_1$-$C_{20}$ alkyl, $C_2$-$C_{20}$ alkenyl, $C_2$-$C_{20}$ alkynyl, or a polyoxyalkylene moiety having oxyalkyl groups that are the same or different, and where $M^+$ is a cation forming a salt; or
$R_1$ and $R_2$ together form a group of formula:

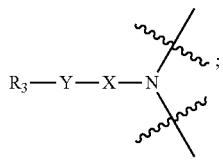

$R_3$ is hydrogen, $C_1$-$C_{20}$ alkyl, $C_2$-$C_{20}$ alkenyl, $C_2$-$C_{20}$ alkynyl, or a polyoxyalkylene moiety having oxyalkyl groups that are the same or different, or $R_3$ is —Z—$R_4$:
wherein Z is $C_1$-$C_{20}$ alkylene, $C_2$-$C_{20}$ alkenylene, $C_2$-$C_{20}$ alkynylene, or a polyoxyalkylene moiety having oxyalkyl groups that are the same or different and $R_4$ is a group of the formula:

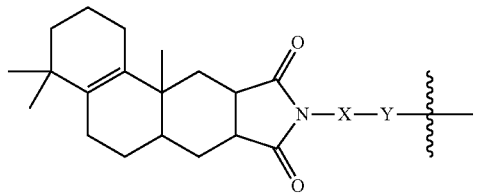

X is independently $C_1$-$C_6$ alkylene, $C_2$-$C_6$ alkenylene, or $C_2$-$C_6$ alkynylene, each optionally substituted with halogen, —OH, $C_1$-$C_6$ alkoxy, —$NO_2$, —CN, —$NH_2$, —NH($C_1$-$C_6$ alkyl), or —$N(C_1$-$C_6$ alkyl)$_2$; and
Y is independently —O—, —NH—, —$N(C_1$-$C_6$ alkyl)-, —C(O)—, —C(O)O—, —C(O)NH—, —$C(O)N(C_1$-$C_6$ alkyl)-, —$S(O)_2$—, or —$S(O)_2O$—.

2. A compound according to claim 1, where $R_1$ and $R_2$ are independently —$OR_5$, —$O^-M^+$, —$NHR_5$, or —$N(C_1$-$C_6$ alkyl)$R_5$;
where $R_5$ is hydrogen, $C_1$-$C_{20}$ alkyl, $C_2$-$C_{20}$ alkenyl, $C_2$-$C_{20}$ alkynyl, or a polyoxyalkylene moiety having oxyalkyl groups that are the same or different; and
$M^+$ is a cation forming a salt.

3. A compound according to claim 2, where
$R_1$ and $R_2$ are independently —$OR_5$ or —$O^-M^+$, where
$R_5$ is hydrogen, $C_1$-$C_{20}$ alkyl, $C_2$-$C_{20}$ alkenyl, $C_2$-$C_{20}$ alkynyl, or a polyoxyalkylene moiety having oxyalkyl groups that are the same or different, and
$M^+$ is a cation forming a salt.

4. A compound according to claim 3, where $R_5$ is a polyoxyalkylene moiety which is polyethylene glycol or methoxypolyethylene glycol.

5. A compound according to claim 1, where $R_1$ and $R_2$ together form a group of formula:

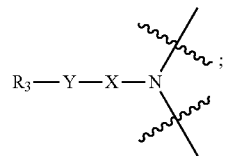

$R_3$ is hydrogen, $C_1$-$C_{20}$ alkyl, $C_2$-$C_{20}$ alkenyl, $C_2$-$C_{20}$ alkynyl, a polyoxyalkylene moiety having oxyalkyl groups that are the same or different, or $M^+$, where $M^+$ is a cation forming a salt, or $R_3$ is —Z—$R_4$:
wherein Z is $C_1$-$C_{20}$ alkylene, $C_2$-$C_{20}$ alkenylene, $C_2$-$C_{20}$ alkynylene, or a polyoxyalkylene moiety having oxyalkyl groups that are the same or different and $R_4$ is a group of the formula:

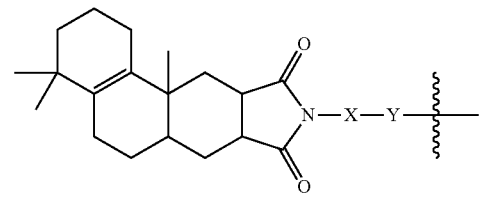

X is independently $C_1$-$C_6$ alkylene, $C_2$-$C_6$ alkenylene, or $C_2$-$C_6$ alkynylene, each optionally substituted with halogen, —OH, $C_1$-$C_6$ alkoxy, —$NO_2$, —CN, —$NH_2$, —NH($C_1$-$C_6$ alkyl), or —$N(C_1$-$C_6$ alkyl)$_2$; and
Y is independently —O—, —NH—, —$N(C_1$-$C_6$ alkyl)-, —C(O)—, —CO(O)O—, —C(O)NH—, —$C(O)N(C_1$-$C_6$ alkyl)-, —$S(O)_2$—, or —$S(O)_2O$—.

6. A compound according to claim 5, where $R_1$ and $R_2$ together form a group of formula:

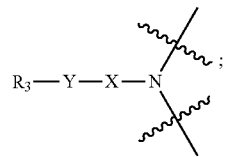

$R_3$ is hydrogen, $C_1$-$C_{20}$ alkyl, $C_2$-$C_{20}$ alkenyl, $C_2$-$C_{20}$ alkynyl, or a polyoxyalkylene moiety having oxyalkyl groups that are the same or different;
X is independently $C_1$-$C_6$ alkylene, $C_2$-$C_6$ alkenylene, or $C_2$-$C_6$ alkynylene, each optionally substituted with halogen, —OH, $C_1$-$C_6$ alkoxy, —$NO_2$, —CN, —$NH_2$, —NH($C_1$-$C_6$ alkyl), or —$N(C_1$-$C_6$ alkyl)$_2$; and
Y is independently —O—, —NH—, —$N(C_1$-$C_6$ alkyl)-, —C(O)—, —C(O)O—, —C(O)NH—, —$C(O)N(C_1$-$C_6$ alkyl)-, —$S(O)_2$—, or —$S(O)_2O$—.

7. A compound according to claim 6, where X is methylene.

8. A compound according to claim 6, where Y is —C(O)O—.

9. A compound according to claim 6, where: X is $C_1$-$C_6$ alkylene; and Y is —C(O)—, —C(O)O—, —C(O)NH—, or —$C(O)N(C_1$-$C_6$ alkyl)-.

10. A compound according to claim 6, where:

X is $C_1$-$C_6$ alkylene; and

Y is —C(O)O—, or —C(O)NH—.

11. A compound according to claim 6, where $R_3$ is a polyoxyalkylene moiety which is polyethylene glycol or methoxypolyethylene glycol.

12. A compound according to claim 1, which is:

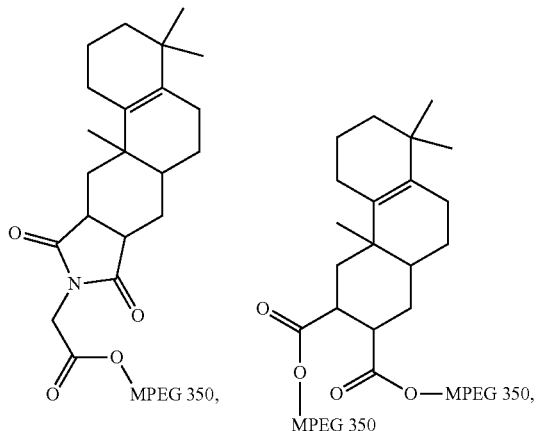

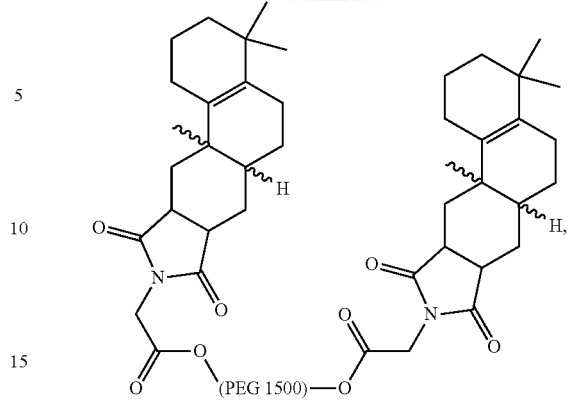

or salts, hydrates, or solvates thereof.

13. A cleaning composition comprising a compound according to claim 1.

14. A surfactant composition comprising a compound according to claim 1.

15. A method of using a compound according to claim 1 in Automatic Dishwashing formulations.

16. A method of using a composition according to claim 13 in Automatic Dishwashing formulations.

17. A compound according to claim 7, where Y is —C(O)O—.

18. A compound of formula:

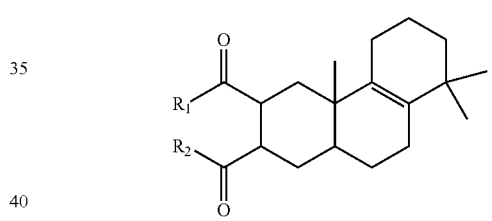

or a regioisomer, salt, solvate, or hydrate thereof; wherein $R_1$ and $R_2$ are independently —$OR_5$, —$O^-M^+$, —$NHR_5$, or —$N(C_1$-$C_6$ alkyl)$R_5$;

where $R_5$ is hydrogen, $C_1$-$C_{20}$ alkyl, $C_2$-$C_{20}$ alkenyl, $C_2$-$C_{20}$ alkynyl, or a polyoxyalkylene moiety having oxyalkyl groups that are the same or different, and where $M^+$ is a cation forming a salt; or $R_1$ and $R_2$ together form a group of formula:

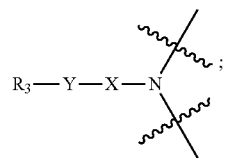

$R_3$ is hydrogen, $C_1$-$C_{20}$ alkyl, $C_2$-$C_{20}$ alkenyl, $C_2$-$C_{20}$ alkynyl, or a polyoxyalkylene moiety having oxyalkyl groups that are the same or different, or $R_3$ is —Z—$R_4$:

wherein Z is $C_1$-$C_{20}$ alkylene, $C_2$-$C_{20}$ alkenylene, $C_2$-$C_{20}$ alkynylene, or a polyoxyalkylene moiety having oxyalkyl groups that are the same or different and $R_4$ is a group of the formula:

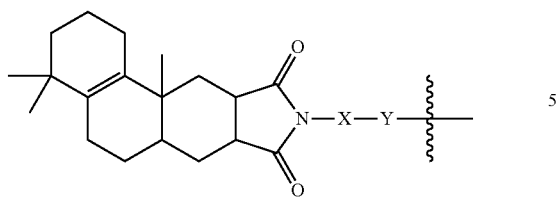
X is independently $C_1$-$C_6$ alkylene, $C_2$-$C_6$ alkenylene, or $C_2$-$C_6$ alkynylene, each optionally substituted with halogen, —OH, $C_1$-$C_6$ alkoxy, —$NO_2$, —CN, —$NH_2$, —NH($C_1$-$C_6$ alkyl), or —N($C_1$-$C_6$ alkyl)$_2$; and
Y is independently —O—, —NH—, —N($C_1$-$C_6$ alkyl)-, —C(O)—, —C(O)O—, —C(O)NH—, —C(O)N($C_1$-$C_6$ alkyl)-, —S(O)$_2$—, or —S(O)$_2$O—.
* * * * *